(12) United States Patent
Zeng et al.

(10) Patent No.: US 10,213,111 B2
(45) Date of Patent: Feb. 26, 2019

(54) METHOD AND APPARATUS FOR OPTICAL MEASUREMENTS UNDER AMBIENT LIGHT CONDITIONS

(71) Applicant: BC Cancer, part of the Provincial Health Services Authority, Vancouver (CA)

(72) Inventors: Haishan Zeng, Vancouver (CA); Jianhua Zhao, Langley (CA); Michael Short, Coquitlam (CA); Thomas Andrew Braun, Richmond (CA)

(73) Assignee: BC Cancer, Part of the Provincial Health Services Authority, Vancouver (CA)

( * ) Notice: Subject to any disclaimer, the term of this patent is extended or adjusted under 35 U.S.C. 154(b) by 346 days.

(21) Appl. No.: 14/766,445

(22) PCT Filed: Feb. 14, 2014

(86) PCT No.: PCT/CA2014/050100
§ 371 (c)(1),
(2) Date: Aug. 6, 2015

(87) PCT Pub. No.: WO2014/124537
PCT Pub. Date: Aug. 21, 2014

(65) Prior Publication Data
US 2015/0366454 A1 Dec. 24, 2015

Related U.S. Application Data

(60) Provisional application No. 61/764,879, filed on Feb. 14, 2013.

(51) Int. Cl.
*A61B 5/00* (2006.01)
*G01J 3/10* (2006.01)
(Continued)

(52) U.S. Cl.
CPC .......... *A61B 5/0071* (2013.01); *A61B 5/0075* (2013.01); *A61B 5/742* (2013.01);
(Continued)

(58) Field of Classification Search
CPC .......... A61B 2560/0247; A61B 5/0071; A61B 5/0075; A61B 5/742; F21K 9/60; G01J 2003/104; G01J 3/10; G01J 3/44
See application file for complete search history.

(56) References Cited

U.S. PATENT DOCUMENTS 9,326,715 B1 * 5/2016 Panasyuk ............. A61B 5/1495

* cited by examiner

*Primary Examiner* — Amanda Hulbert
(74) *Attorney, Agent, or Firm* — Oyen Wiggs Green & Mutala LLP

(57) ABSTRACT

Examples of a spectroscopy system with a specially design ambient illumination system are disclosed. The ambient illumination system comprises one or more light emitting diodes (LEDs) that provide illumination light in the wavelength of 400-785 nm. The ambient illumination system can further comprise a filter to block light above 785 nm. The filter can be placed directly in front of LED emitters. The LEDs can be white LEDs or RGB LEDs. The spectroscopy system can further comprise a control system that can receive a signal from the spectral probe when the spectral measurements commence and can instantaneously send a signal to automatically switch off the ambient illumination system and to receive a signal from the spectral probe when the spectral measurements are terminated and automatically switch on the ambient illumination system. Examples of methods of operating the spectroscopy system and the ambient illumination system are disclosed.

9 Claims, 7 Drawing Sheets

(51) Int. Cl.
*G01J 3/44* (2006.01)
*F21K 9/60* (2016.01)
(52) U.S. Cl.
CPC ............... *F21K 9/60* (2016.08); *G01J 3/10* (2013.01); *G01J 3/44* (2013.01); *A61B 2560/0247* (2013.01); *G01J 2003/104* (2013.01)

METHOD AND APPARATUS FOR OPTICAL MEASUREMENTS UNDER AMBIENT LIGHT CONDITIONS

The present disclosure relates generally to a method and apparatus for optical measurements performed under an ambient light as passive lighting used into examination room and more particularly relates to a spectroscopy system with an ambient illumination system for spectral measurements performed under ambient light conditions.

BACKGROUND

Optical imaging systems and methods which provide real-time detection, diagnosis and imaging of diseases are known in the art. The application of such systems in vivo during real time medical procedures has been limited by a poor signal to noise ratio. The low signal to noise ratio is a consequence of the low strength or absence of an optical signal coming from the target tissue and a high level of background noise from any ambient light. In order to improve the signal to noise the majority of known optical diagnostic systems and methods block the ambient light, ignore it, background subtracting it or turn off room light during measurements. However, turning off the lights or obscuring a view of the patient during a medical procedure can be disadvantageous and possibly dangerous. On the other hand by simply ignoring or background subtracting ambient light, one risk to overflow the detector and/or bury the weak signals of a tissue in the background noise unless the ambient light is specifically rejected. Some other known system and method for rejecting ambient light include gating the detector or modulate the illumination signal and using lock-in detection. However, some of these methods are not applicable to measure weak Raman signals that require continuous integration of the signal for one to several seconds or minutes, in some instances.

Some spectroscopy examination procedures such as for example, Raman spectral measurements or fluorescence spectroscopy can be very sensitive to contamination from the ambient light because Raman or fluorescence signals can be extremely weak and even a small leak of ambient light can impede with the signal. Raman spectroscopy is a spectroscopic technique that operates on the principle that light of a single wavelength striking a molecule is scattered by the molecule through a molecular vibration state transition. The resultant scattered light has wavelengths different than the incident or excitation light. The wavelengths present in the scattered light are characteristic of the structure of the molecule. The intensity and wavelength or "Raman Shift" of the scattered light is representative of the concentration of the molecules in the sample. So, the spectrum of the inelastically scattered radiation represents a fingerprint of the molecular vibrations within the observed sample. Traditionally, the excitation light source, typically a laser, is directed continuously against a target tissue, and the Raman signal is collected over time. In addition to the fact that the Raman signal is naturally very weak, a further problem is the interference with the fluorescence signal due to tissue fluorescence, or emission of light. Many compounds fluoresce or emit light when exposed to laser light in the visible region. Fluorescence bands are generally broad and featureless, and the Raman signal can be often obscured by the fluorescence.

Therefore, there is a need for a system with shaped ambient illumination so that Raman measurements can be carried out under such ambient illumination.

SUMMARY

In one aspect, an ambient illumination system for spectral measurements is provided. The ambient illumination system comprises one or more light emitting diodes (LEDs) to generate ambient light in the area during spectral measurements and a control system that is configured to produce an output signal to the one or more LEDs such that during spectral measurements the one or more LEDs are turned off. The control system can further be configured to produce a trigger signal to the one or more LEDs to turn them on once the spectral measurements are completed.

In another aspect, the ambient illumination system comprises one or more optimized RGB LEDs. The RGB LEDs are optimized such that the red LED generates light in a 620-680 nm wavelength range.

In one aspect, a filter is provided configured to pass visible components of the ambient illumination light and to block near infrared (NIR) component of the ambient illumination light. The filtered illumination light of the one or more LEDs provide an illumination light in the wavelength of 400-780 nm.

In another aspect, a spectroscopy system with an ambient illumination system is provided. The spectroscopy system comprises a spectroscopy probe, a light source for providing illumination light to a subject under examination, a detector to receive a returned radiation reflected and emitted from the subject and to measure a spectrum of the returned radiation, a display in communication with the detector to display the measured spectrum and one or more light emitting diodes (LEDs) to generate ambient light in the area during spectral measurement.

In one aspect, a control system is provided configured to control the light source and the one or more LEDs such that when the light source is turned on the one or more LEDs are turned off. The control system further comprises a switch to turn on the light source and automatically to produce a signal transmitted to the one or more LEDs to turn them off. The control unit can further communicate with the detector to receive an input signal from the detector when the detector detects the returning radiation and automatically produces an output signal to the one and more LEDs to turn them on. In addition, the control unit can control the display to turn it off when the light source is on.

In another aspect, the spectroscopy system further comprises a filter configured to pass visible components of the ambient illumination light and to block near infrared (NIR) component of the ambient illumination light.

In another aspect, the one or more LED of the ambient illumination light are optimized RGB LEDs.

In addition to the aspects and embodiments described above, further aspects and embodiments will become apparent by reference to the drawings and study of the following detailed description.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure. Sizes and relative positions of elements in the drawings are not necessarily drawn to scale. For example, the shapes of various elements and angles are not drawn to scale, and some of these elements are arbitrarily enlarged and positioned to improve drawing legibility.

FIG. 4 is a graph of a background signal when a laser of a spectroscopy system of FIG. 3 is turned off and an LED ambient lamp without any filter to shape the ambient light is turn on.

DETAILED DESCRIPTION OF SPECIFIC EMBODIMENTS

The present invention provides a system for providing ambient light in an examination room during real-time in vivo spectral measurements and more specifically during in vivo Raman spectral measurements.

Definitions

For the purposes of this invention, the following definitions are provided:

Ambient Light: The background light incident upon a subject. The ambient light may include at least room light, overhead lamps, lights from monitor, and other light sources.

Signal to Noise: The ratio of the strength of a target signal to the background noise. This can be increased either by improving the target signal, or by reducing the background noise.

Real Time: A measurement performed in few seconds or less, and preferably in 1 second, that allows a procedure or a treatment plan to be modified based upon the results of the measurement.

Subject: A living animal, plant, viral, or bacterial subject, with an emphasis on mammals, especially humans.

In Vivo: A measurement performed on tissues within a living subject.

Figure 1A:
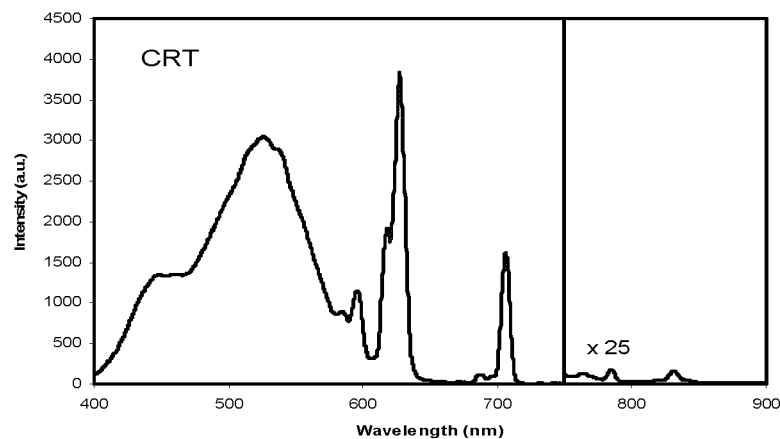
FIG. 1a is a graphical illustration of an output spectrum of a cathode ray tube (CRT) monitor.
Figure 1B:
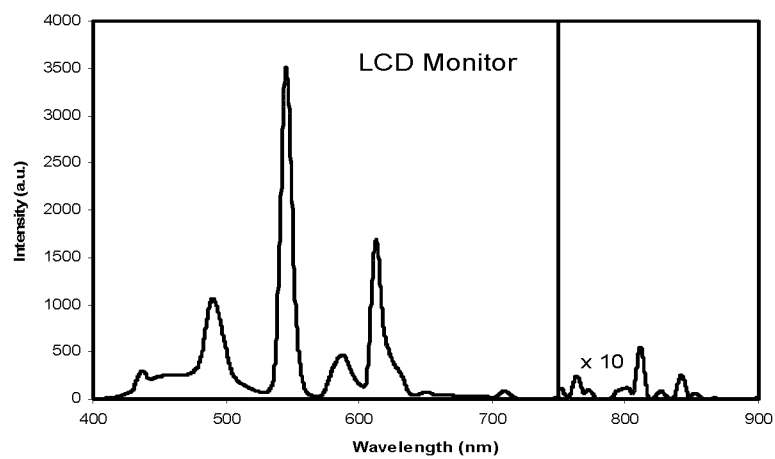
FIG. 1b is a graphical illustration of an output spectrum of a liquid crystal display (LCD) monitor.
Figure 1C:
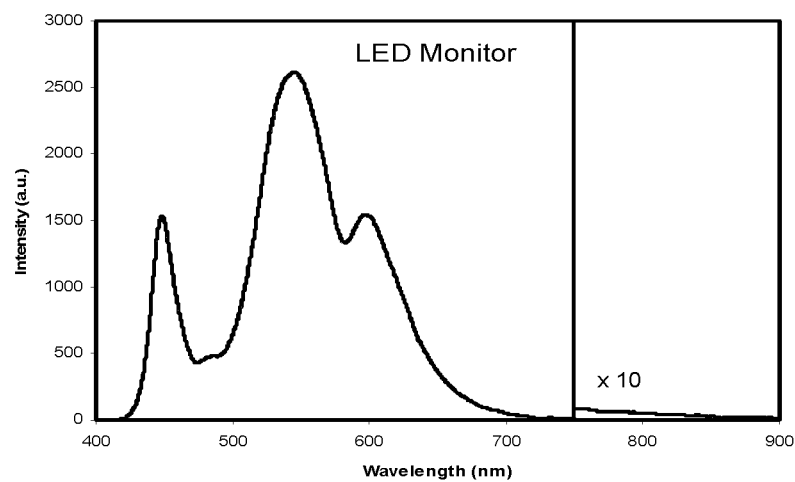
FIG. 1c is a graphical illustration of an output spectrum of a light emitting diode (LED) monitor.

Naturally Raman signals are very weak and even if the room light is off, light from a system's monitor can be strong enough to contaminate the Raman signal. This can be shown clearly in FIG. 1a-c. FIG. 1a illustrates an output spectrum of a CRT monitor. The signal in the 700-900 nm waveband is amplified by 25 times to better visualize the signal.

As can be noticed there are two peaks in the 785-1000 nm range that are strong enough to contaminate the Raman signal in this range. With respect to an output spectrum from an LCD monitor illustrated in FIG. 1b, it can be noticed that there are a number of peaks in the 785-1000 nm range that are strong enough to contaminate the Raman signal in this range. The signal in the 750-900 nm waveband range is amplified 10 times to better visualize the signal. The experiments have shown that LED backlighting LCD monitor, so called LED monitor (FIG. 1c) has provide best of the three monitors output spectrum from a point of spectral measurements. As can be noticed from an output spectrum of the LED monitor shown in FIG. 1c, there are no peaks in the 785-1000 nm range, however, the tail in the 785-1000 nm can potentially be strong enough to affect fluorescence background, which in turn can affect Raman signal in this range. The signal in the 750-900 nm waveband range is amplified 10 times to better visualize the signal. The experiments have also shown that the output spectra of fluorescence room lamp in the waveband of 750-900 nm range includes a number of peaks in the 785-1000 nm that are strong enough to contaminate the Raman signal in this range and thus fluorescence lamp should not be used for room lightening for Raman measurements.

Figure 2:
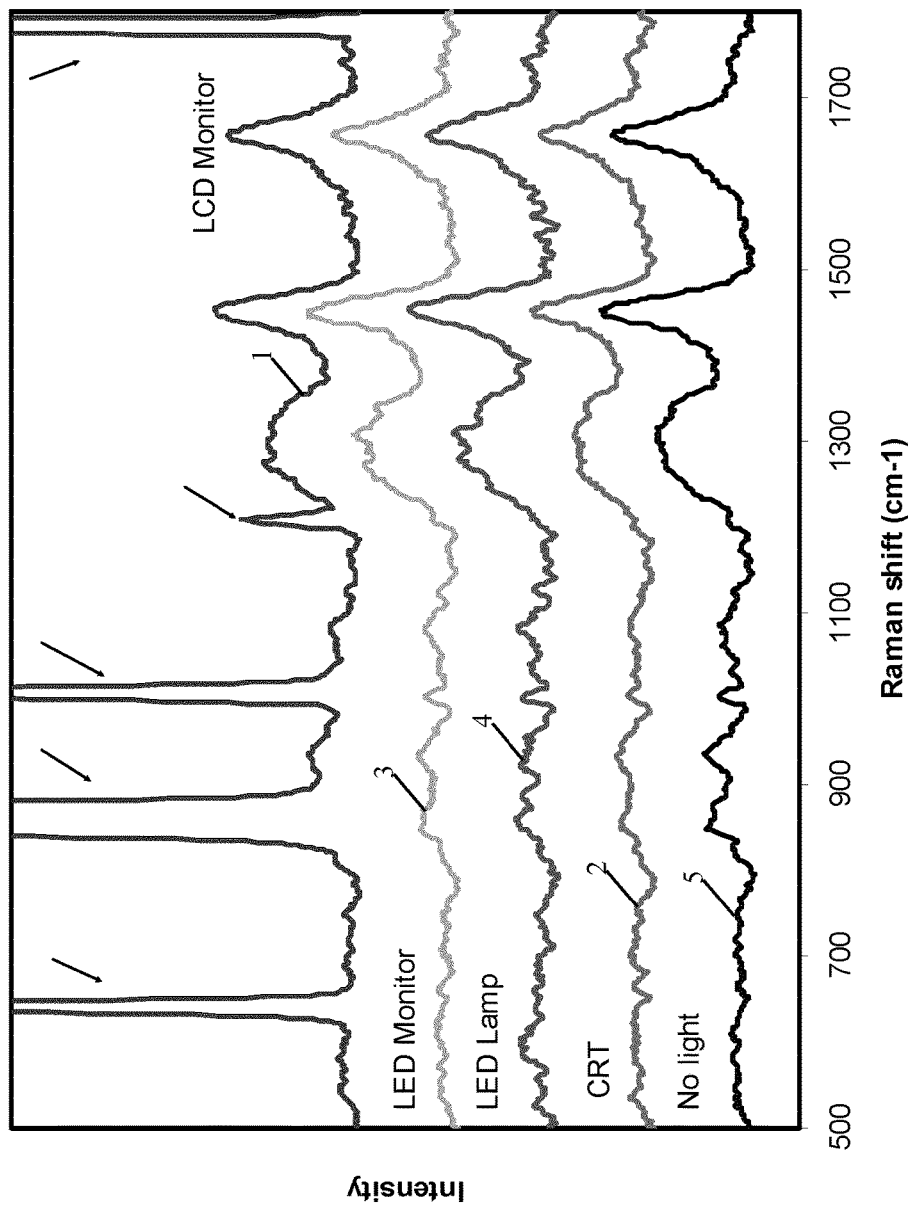
FIG. 2 is graph of a Raman spectrum of palm skin with a different ambient lighting.

FIG. 2 illustrates a Raman spectrum of palm skin with different ambient illumination. As it can be seen when the Raman measurements are taken with LCD monitor, shown with curve 1, there are a number of huge artificial peaks (see the peaks marked with arrows) which can contaminate the Raman signal. There are 1-2 artificial peaks with CRT monitor (curve 2), but the Raman signal is relatively weak and is buried by the background signal. Raman measurements with LED monitor/LED lamp as ambient light shown with curve 3 and curve 4, respectively, seem to produce reasonable results. As can be noticed from curves 3 and 4, there are noticeable Raman signals in the 785-1000 nm range. As it is expected, the Raman measurement with no ambient lighting, no room light, as represented by curve 5, shows the best results for Raman signal.

Several different LED light sources were assessed for providing ambient light during Raman spectral measurements. For example, a white LED lamp containing phosphor materials, such as SYLVANIA™ LED Lamp, PHILIPS™ LED Lamp or OHM™ LED Lamp or any other type of white LED lamp can be used. In one embodiment, 3 color LED Lamp (RGB) with no phosphor materials, such as MCL™ 3 color LED Lamp with controller to change color combinations, were tasted. It has been found that white LED lamp with phosphor materials can provide tail signals beyond 750 nm that can contaminate the Raman signal. Also for 400-500 nm signals, it was found that there will be second order diffraction for 800-1000 nm wavelength range if the signal is not properly filtered in the Raman system. In addition, it was found that when using a long pass filter, i.e a RS 785 LP filter (Semrock, Rochester, N.Y.), the filter can block some of the LED light and the 785 nm Raman excitation light, but not the signal above 785 nm, particularly when this filter is used with white light LED lamps. The tested long pass filter cannot block 400-750 nm light that can cause problems for Raman measurement and therefore as such if used for filtering the ambient lighting during Raman measurements it can impede the Raman signal. Even when the LED lamp is not close to the Raman probe there is a LED signal leakage which can contaminate the measured Raman spectrum. The LED leakage can become bigger when the probe is close to the LED ambient lamp.

The present invention describes a system for producing an ambient light for Raman measurements by shaping the LED lamp spectrum. In one implementation, a band-pass filter can be used to trim off near infrared (NIR) components of the ambient light. A visible LED spectrum of the ambient light can be blocked by providing a long-pass filter before a detector of a Raman system. For example, a BLP01-785R long-pass filter (Semrock, Rochester, N.Y.) can be used in the Raman system to reject the LED ambient illumination from 300-785 nm. This is only for illustrating purposes and any other long-pass filter can be used in the Raman system.

Figure 3:
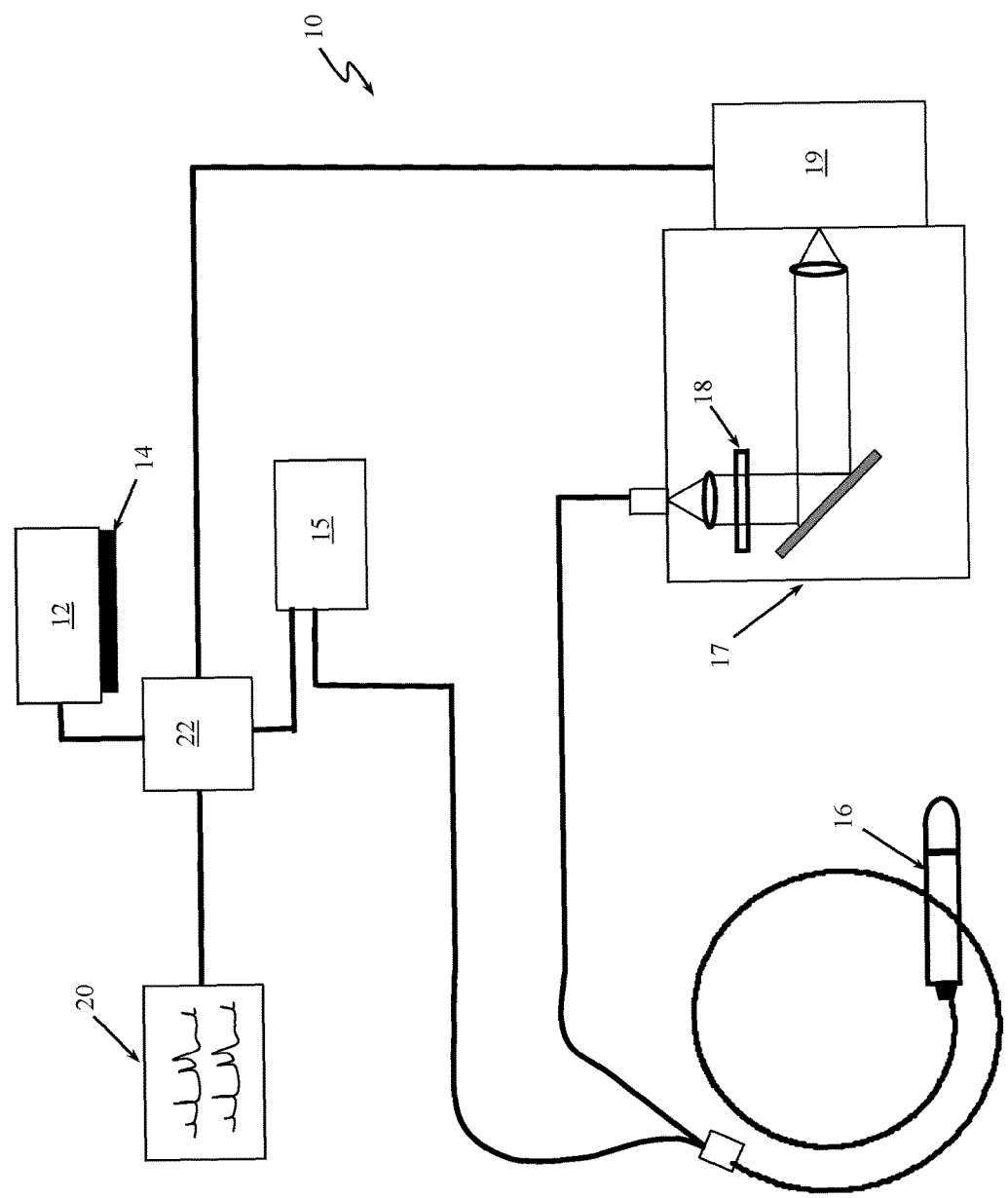
FIG. 3 is a schematic view of an example of a spectroscopy system using an embodiment of an ambient illumination system of the present invention.

FIG. 3 shows a Raman system 10 and a LED ambient illumination system 12. The LED ambient light can be shaped using a filter 14. In one implementation, the filter 14 can be put directly in front of the LED emitter to reduce a filter size. The Raman system 10 can further comprise a probe 16 and a laser 15 to provide an illumination light to a target subject of examination. Light reflected or emitted from the target is directed to a spectrograph 17 and is detected by a detector 19. A long-pass filter 18 can be provided to prevent the light in a visible range, 300-785 nm range, to reach the spectrograph 17. The detector 19 can be pixelated detector, such as a charge coupled device (CCD), a charge injection device (CID), an intensified CCD detector, a photomultiplier tube (PMT) detector array, a photodiode array (PDA), an intensified PDA, etc. The signal from the detector 19 can be processed, analyzed and displayed on a monitor 20. The monitor can be a LED monitor.

Figure 4:
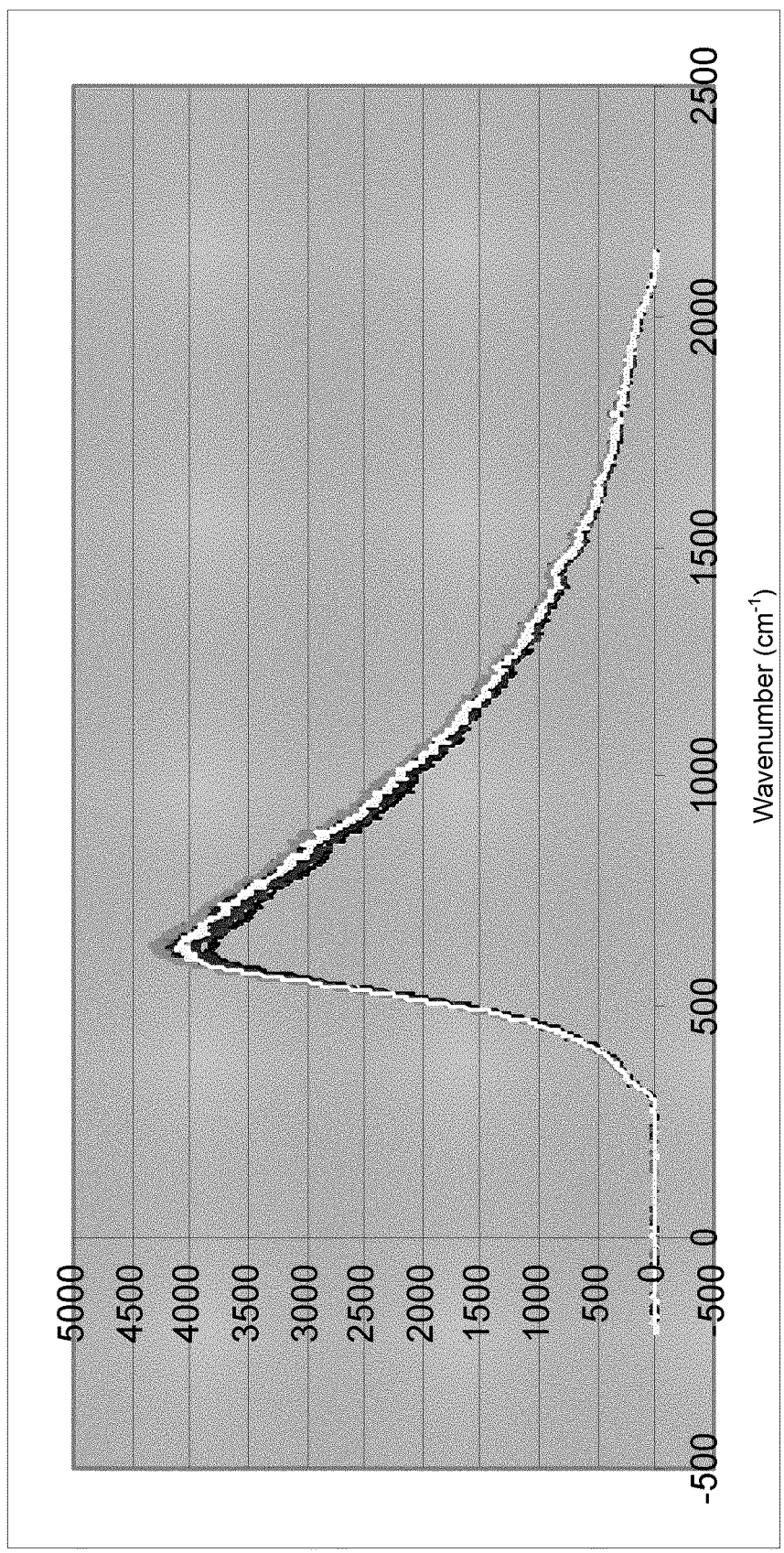

FIG. 4 graphically illustrates a background signal when no filter 14 is used with the LED ambient light source 12. In the graph shown in FIG. 4 the Raman system's light source such as a laser 15 of FIG. 3 is turned off while the LED ambient lamp 12 is still on. As can be noticed there is a leakage of the LED light into the system. Also there can be leakage from the monitor 20, however comparing with the LED ambient light leakage, the peaks from the monitor can be weaker and thus not clearly seen in the graph.

Figure 5:
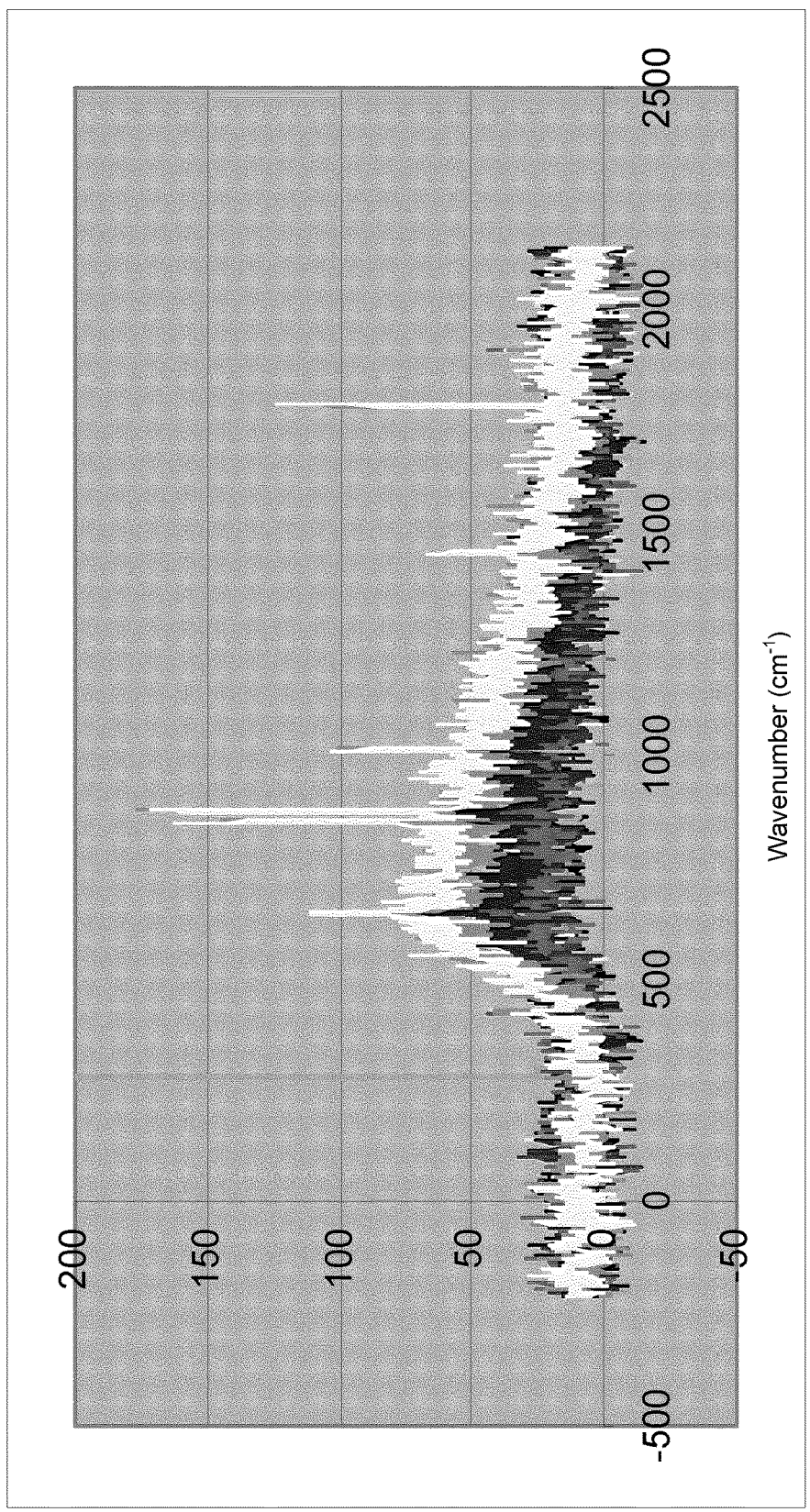
FIG. 5 is a graph of a background signal of FIG. 4 when a filter is placed before a LED ambient light to shape the ambient light.

FIG. 5 shows the same experiment as in FIG. 4, but here we placed a band pass filter in front of the LED ambient lamp. For illustrative purposes only, the filter can be a BG39 or a BG40 band pass filter mounted in front of the LED lamp. As can be noticed from the graph in FIG. 5 the leakage of LED lamp signal is greatly reduced.

Figure 6:
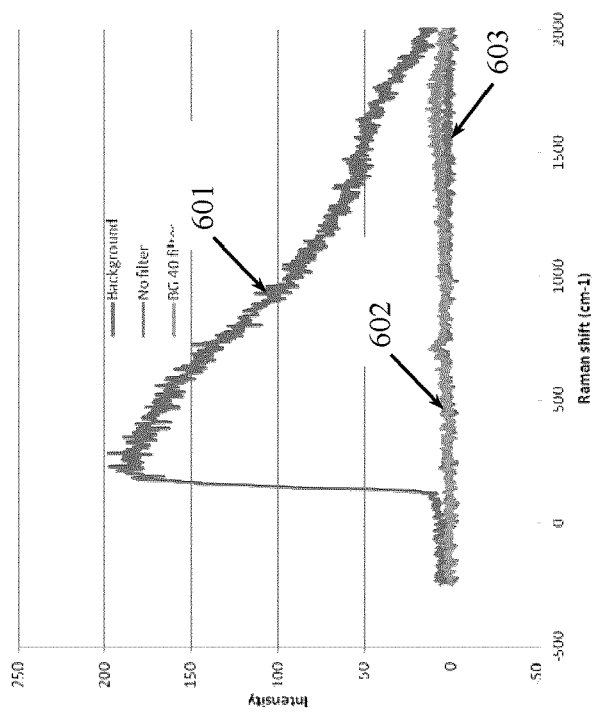
FIG. 6 is a graph of emission spectra of two types of LEDs in a Raman wavelength range without any filter in front of a LED ambient light (curve 601) and with a filter mounted in front of a LED ambient light to shape the ambient light (curve 602). The figure also shows emission spectrum of a background signal (curve 603).
Figure 6:
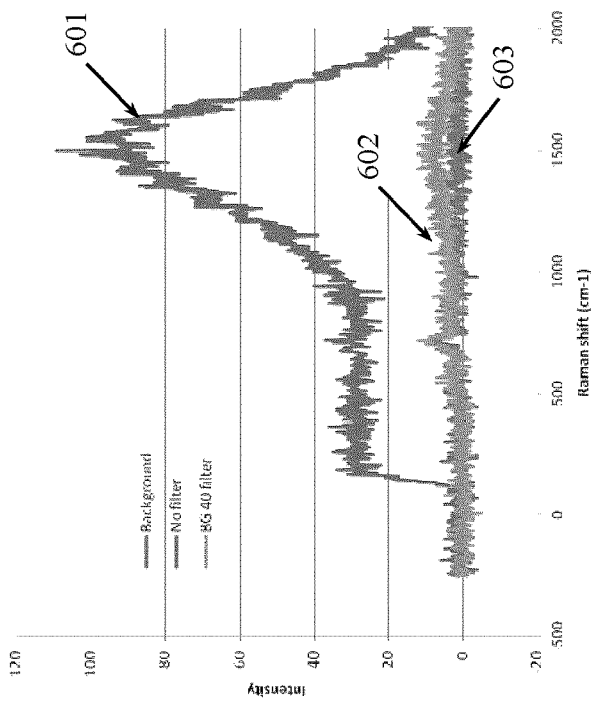

FIG. 6 illustrates emission spectra of two types of LEDs in the Raman wavelength range. Curve 601 shows the emission spectra of the LED ambient light when there is no filter in front of the LED light. Curve 602 illustrates the emission spectrum of the LED ambient light when there is a band-pass filter mounted in front of the LED light and curve 603 is emission spectrum of the background signal when the LED ambient light is turned off. As can be noticed, there are tail signals from the LED lamp when there is no filter in front of the LED that can cause a contamination of the Raman signal. After applying the filter, the LED tails can be prevented. In the graph shown in FIG. 6 it looks that tail is not completely prevented by applying the filter in front of the LED. It was learned that the reason for the possible tail is the fact that the long-pass filter that was used in the Raman probe during the experiment cannot completely reject the visible waveband of the LED light. The residuals are actually from the second order diffraction of the blue-yellow part of the LED lamp that is out of the scope of the long-pass filter however, this can be prevented by switching to a long-pass filter that can block this band of the visible range. As mentioned herein before, in the experiments presented in some of the graphs shown herein, we have used BG-39 and/or BG 40 as a band-pass filter mounted in front of the LED light however, these filters cut some red waveband components which can have an effect on the ambient lightening in the examination room making an unnatural perception for an operator.

Figure 7:
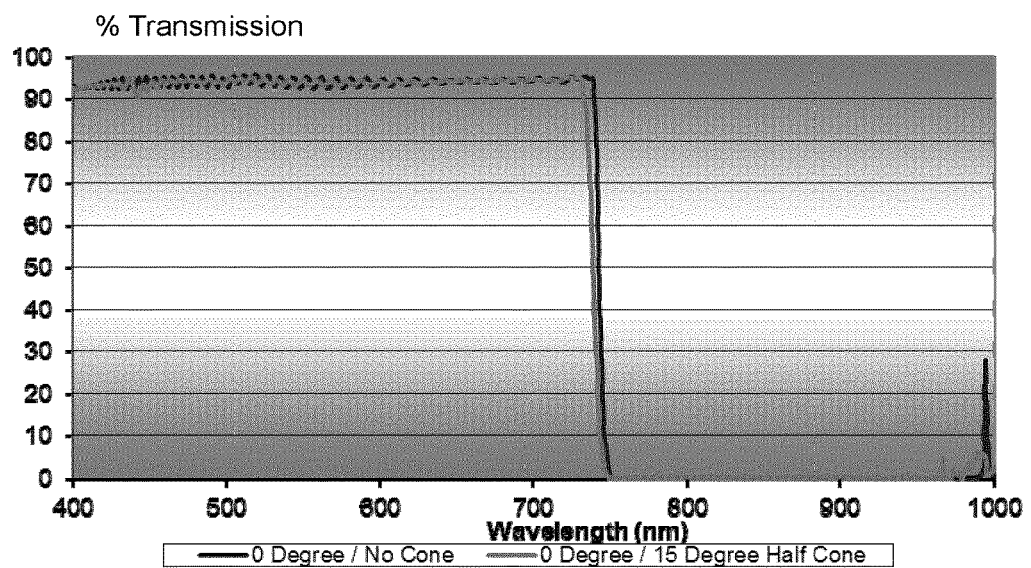
FIG. 7 graphically illustrates a transmission characteristics of a filter mounted in front of a LED ambient light to shape the ambient light.
Figure 7:
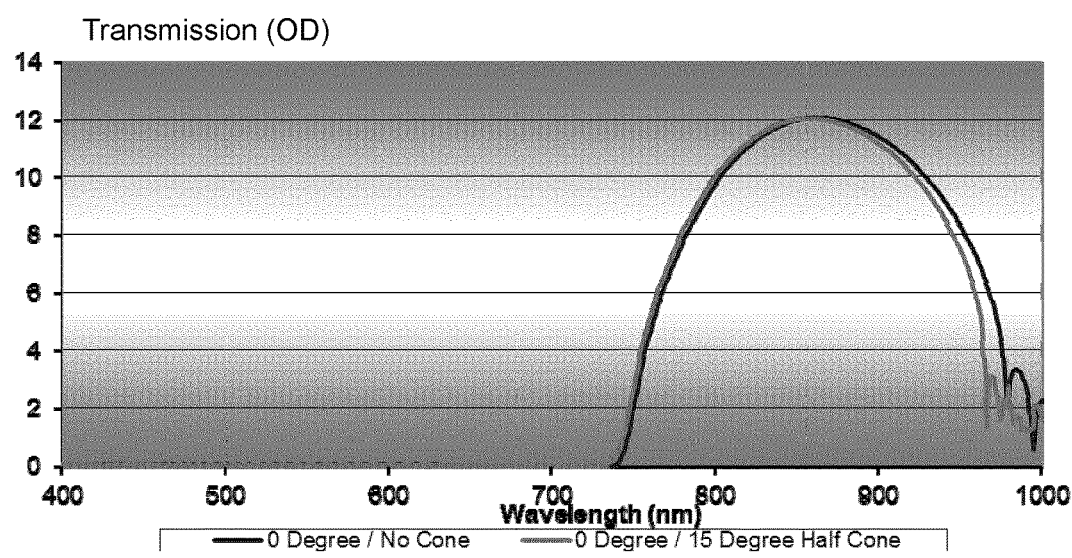

FIG. 7 shows transmission curves of another embodiment of a band-pass filter mounted in front of the LED light which can preserve all visible components of the LED light while can block the near infrared (NIR) components which can contaminate the Raman signals. This filter can be an interference type of filter, assuming that the LED light half cone angle is 15 degrees.

By using a shaped LED lamp ambient illumination, Raman measurements can be carried out under ambient illumination. The LED light source can comprise a white LED with phosphor material or an RGB 3-LED lamp without phosphor materials (e.g. MCL™ RGB LEDs). Surprisingly the experiments have shown that the RGB 3-LED Lamp without phosphor materials can still provide NIR components that can affect Raman measurements thus a filter is still needed with the lamp if used for Raman measurements.

The NIR components can be generated by epoxy materials or the enclosure materials used in the RGB 3-LED lamp.

In one implementation, the LED light source can comprise a RGB 3-LED Lamp which is optimized so that no NIR components are generated thus the ambient lighting can be provided with this optimized RGB 3-LED lamp without using a filter to cut the NIR components from the light. The RGB 3-LED lamp can be optimized such that the RGB LED lamp is blue shifted compared to the standard RGB LEDs so that it can produce light below 780 nm and no light in the NIR range is emitted even though no filter is used. For example, the red LED lamp can be optimized to generate illumination light in the 620 -680 nm wavelength range.

In another implementation, the ambient light can be connected to a control system 22 (FIG. 3) of the spectroscopy system. The control system 22 may include one or more processors, controllers, or general or special purpose computing hardware. In various implementations, the control system can control the ambient lightening system 12, e.g. the one or more LEDs and/or the monitor 20. The control system receives as an input signal a signal from the laser 15 when the laser 15 is turned on. Based on such input signal from the laser 15 the control signal can produce an output signal that it transmits to the ambient light system 12 to turn the one or more LEDs off. So, the subject under examination can be inspected under the ambient lighting. When an operator wants to take spectral measurement of an area of interest a spectral measurement switch (not shown) can be pressed which can trigger the laser 15 and the control system 22. The control system can then send a signal to the ambient light source 12 to turn off the ambient light. For example, the ambient light can be switched off for a predetermined time, e.g. one or two seconds. In one example, once a signal of the spectral measurements is detected by the detector 19, the detector 19 will send a signal to the control system 22. Based on such signal that the control system 22 receives from the detector it can generate a signal to the ambient lightening system 12 to switch it on again. This can actually provide a way to tell the operator that the measurements have been completed. In one embodiment, the control system 22 can send a signal to a power system of the monitor 20 to automatically turn off the monitor 20 during the spectral measurements and to turn it on once the spectral measurements have been completed. The control system 22 can include or be in communication with one or more computer-readable storage media that can be used to store, persistently or otherwise, the control information. Since the control system 22 controls the operation of the ambient light system 12 such that the ambient light is turned off during the spectral measurements the filter for shaping the ambient light can be avoided.

Embodiments of a LED ambient illumination (lightening) system used during optical detection procedures are disclosed. Any of the embodiments of the LED ambient illumination system can be used for Raman measurements on skin or any internal organs. In some implementations, the ambient illumination system of the present invention can be for fluorescence measurements of internal organs. For example, the shaped LED ambient light can be used for illumination to guide a fluorescence or Raman spectrum and/or imaging measurements. In some implementations, any of the disclosed LED ambient lightening system can be used as a room lightening in the examination rooms.

While particular elements, embodiments and applications of the present disclosure have been shown and described, it will be understood, that the scope of the disclosure is not limited thereto, since modifications can be made without departing from the scope of the present disclosure, particularly in light of the foregoing teachings. Thus, for example, in any method or process disclosed herein, the acts or operations making up the method/process may be performed in any suitable sequence and are not necessarily limited to any particular disclosed sequence. Elements and components can be configured or arranged differently, combined, and/or eliminated in various embodiments. The various features and processes described above may be used independently of one another, or may be combined in various ways. All possible combinations and subcombinations are intended to fall within the scope of this disclosure. Reference throughout this disclosure to "some embodiments," "an embodiment," or the like, means that a particular feature, structure, step, process, or characteristic described in connection with the embodiment is included in at least one embodiment. Thus, appearances of the phrases "in some embodiments," "in an embodiment," or the like, throughout this disclosure are not necessarily all referring to the same embodiment and may refer to one or more of the same or different embodiments. Indeed, the novel methods and systems described herein may be embodied in a variety of other forms; furthermore, various omissions, additions, substitutions, equivalents, rearrangements, and changes in the form of the embodiments described herein may be made without departing from the spirit of the inventions described herein.

Various aspects and advantages of the embodiments have been described where appropriate. It is to be understood that not necessarily all such aspects or advantages may be achieved in accordance with any particular embodiment. Thus, for example, it should be recognized that the various embodiments may be carried out in a manner that achieves or optimizes one advantage or group of advantages as taught herein without necessarily achieving other aspects or advantages as may be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without operator input or prompting, whether these features, elements and/or steps are included or are to be performed in any particular embodiment. No single feature or group of features is required for or indispensable to any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

The example calculations, simulations, results, graphs, values, and parameters of the embodiments described herein are intended to illustrate and not to limit the disclosed embodiments. Other embodiments can be configured and/or operated differently than the illustrative examples described herein. Indeed, the novel methods and apparatus described herein may be embodied in a variety of other forms; furthermore, various omissions, substitutions and changes in the form of the methods and systems described herein may be made without departing from the spirit of the inventions disclosed herein.

The invention claimed is:

1. A spectroscopy system, the system comprising:
a spectroscopy probe;
a light source producing an illumination light to illuminate a subject under examination and to produce returning radiation;
a detector coupled to capture the returned radiation and measure a spectrum of the returned radiation;
a display in communication with the detector to display the measured spectrum;
an ambient light illumination source comprising one or more light emitting diodes (LEDs) to generate ambient light in a surrounding area where a spectral measurement is taken; and
a control system in communication with the light source and the display, the control system being configured to receive an input signal from the light source when the light source is on and to produce an output signal to turn off the display during the spectral measurements.

2. The spectroscopy system of claim 1, wherein the control system is in communication with the ambient light illumination source, the controller producing an output signal to the ambient light illumination source to turn it off upon a receipt of the input signal from the light source.

3. The spectroscopy system of claim 2, wherein the control system further comprises a switch in communication with the control system to simultaneously activate the light source and deactivate the one or more LEDs.

4. The spectroscopy system of claim 2, wherein the control unit further communicates with the detector such that when the detector detects the returning radiation the control system produces an output signal to the one and more LEDs to turn them on.

5. The spectroscopy system of claim 1, further comprises a filter configured to pass visible components of the ambient illumination light and to block near infrared (NIR) component of the ambient illumination light.

6. The spectroscopy system of claim 5, wherein the filter is configured to cut out the light with wavelength above 780 nm.

7. The spectroscopy system of claim 5, wherein the filter is mounted directly in front of the one or more LEDs.

8. The spectroscopy system of claim 1, wherein the one or more LEDs are optimized RGB LEDs, the red LED being shifted to generate light in a 620-680 nm wavelength range.

9. The spectroscopy system of claim 1, further comprising a long pass filter placed before the detector configured to block light bellow 785 nm wavelength and pass light above 785 nm wavelength.

\* \* \* \* \*